US00PP14493P29

(12) United States Plant Patent
Sakazaki

(10) Patent No.: US PP14,493 P2
(45) Date of Patent: Jan. 27, 2004

(54) PETUNIA PLANT NAMED 'CONDOLAVENDER'

(50) Latin Name: *Petunia×hybrida*
Varietal Denomination: Condolavender

(75) Inventor: Ushio Sakazaki, Shiga (JP)

(73) Assignee: Plant ZI LLC, San Marco, CA (US)

( * ) Notice: Subject to any disclaimer, the term of this patent is extended or adjusted under 35 U.S.C. 154(b) by 0 days.

(21) Appl. No.: 10/385,247

(22) Filed: Mar. 10, 2003

(51) Int. Cl.[7] ..... A01H 5/00

(52) U.S. Cl. ..... Plt./356

(58) Field of Search ..... Plt./356

(56) References Cited

U.S. PATENT DOCUMENTS

PP12,012 P2 * 7/2001 Brown ..... Plt./356

OTHER PUBLICATIONS

UPOV ROM GTITM Computer Database, GTI JOUVE Retrieval Software 2003/02 citation(s) for 'Condolavender'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Petunia plant named 'Condolavender', characterized by its outwardly spreading and uniform plant habit; freely branching habit; numerous double flowers that are light lavender in color; and good garden performance.

1 Drawing Sheet

Botanical classification/cultivar designation: *Petunia×hybrida* cultivar Condolavender.

BACKGROUND OF THE INVENTION

The present Invention relates to a new and distinct cultivar of Petunia plant, botanically known as *Petunia×hybrida,* and hereinafter referred to by the cultivar name Condolavender.

The new Petunia is a product of a planned breeding program conducted by the Inventor in Shiga Prefecture, Japan. The objective of the breeding program is to create new outwardly spreading Petunias with numerous double flowers with attractive flower colors.

The new Petunia originated from a cross made by the Inventor in April, 1999 of an unidentified Brazilian single-flowered selection of Petunia, not patented, as the female, or seed parent, with an unidentified lavender-colored double-flowered selection of Petunia, not patented, as the male, or pollen parent. The new Petunia was selected as a single plant from the resulting progeny on Oct. 20, 1999 in Gensingen, Germany, on the basis of its numerous double flowers.

Asexual reproduction of the new cultivar by terminal vegetative cuttings since November, 1999, taken in Gensingen, Germany has shown that the unique features of this new Petunia are stable and reproduced true to type in successive generations.

SUMMARY OF THE INVENTION

Plants of the cultivar of Condolavender have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Condolavender'. These characteristics in combination distinguish 'Condolavender' as a new and distinct cultivar:

1. Outwardly spreading, cascading and uniform plant habit.
2. Freely branching habit.
3. Numerous double flowers that are light lavender in color.
4. Good garden performance.

Plants of the new Petunia differ from plants of the female parent, the unidentified Brazilian single-flowered selection, in the following characteristics:

1. Plants of the new Petunia have larger flowers than plants of the female parent.
2. Plants of the new Petunia have double flowers whereas plants of the female parent have single flowers.

Plants of the new Petunia differ from plants of the male parent, the unidentified lavender-colored double-flowered Petunia selection, in the following characteristics:

1. Plants of the new Petunia are more outwardly spreading and not as upright as plants of the male parent.
2. Plants of the new Petunia are more vigorous and more freely branching than plants of the male parent.
3. Plants of the new Petunia have better garden performance than plants of the male parent.

Plants of the new Petunia can be compared to plants of the cultivar Cobink, disclosed in U.S. Plant Pat. No. 12,012. In side-by-side comparisons conducted in Gensingen, Germany, plants of the new Petunia differed from plants of the cultivar Cobink in the following characteristics:

1. Plants of the new Petunia were more outwardly spreading and not as upright as plants of the cultivar Cobink.
2. Plants of the new Petunia had larger flowers than plants of the cultivar Cobink.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Petunia.

The photograph at the top of the sheet comprises a side perspective view of a typical flowering plant of 'Condolavender' grown in a 15-cm container.

The photograph at the bottom of the sheet comprises a close-up view of typical flowers and leaves of 'Condolavender'.

DETAILED BOTANICAL DESCRIPTION

The aforementioned photographs and following observations and measurements describe plants grown in Bonsall, Calif., in an outdoor nursery during the winter under full sun conditions with day temperatures ranging from 18 to about 35° C. and night temperatures ranging from 7 to 18° C. After planting rooted cuttings, plants were grown for about nine weeks in 15-cm containers. Color references are made to The Royal Horticultural Society Colour Chart, 1995 edition, except where general terms of ordinary dictionary significance are used.

Botanical classification: *Petunia×hybrida* cultivar Condolavender.

Parentage:

*Female parent.*—Unidentified Brazilian single-flowered *Petunia ×hybrida* selection, not patented.

*Male parent.*—Unidentified lavender-colored double-flowered *Petunia×hybrida* selection, not patented.

Propagation:

*Type cutting.*—Terminal vegetative cuttings.

*Time to initiate roots, summer and winter.*—About 15 days at 20 to 22° C.

*Time to develop roots, summer and winter.*—About 20 days at 18 to 20° C.

*Root description.*—Fine; white, close to 155D, in color.

*Rooting habit.*—Freely branching.

Plant description:

*Form.*—Annual flowering plant; indeterminate; initially upright, then outwardly speading and trailing; uniform. Freely branching habit with about eight lateral branches per plant.

*Usage.*—Appropriate for hanging baskets, window boxes, patio containers and landscape applications.

*Plant height.*—About 8 cm.

*Plant diameter.*—About 48 cm.

*Vigor.*—Vigorous.

*Lateral branches.*—Length: About 28 cm. Diameter: About 5 mm. Internode length: About 2 cm. Texture: Pubescent. Color: 144B.

*Foliage description.*—Arrangement: Alternate before flowering; opposite after flowers develop; simple. Quantity per lateral branch: About 26 to 28. Length: About 5.8 cm. Width: About 4.5 cm. Shape: Elliptic to obovate. Apex: Broadly acute. Base: Attenuate. Margin: Entire. Texture, upper and lower surfaces: Pubescent; glandular. Venation pattern: Pinnate, arcuate. Color: Developing leaves, upper surface: 146A. Developing leaves, lower surface: 146B. Fully expanded leaves, upper surface: 147A. Fully expanded leaves, lower surface: 147B. Venation, upper surface: 146C. Venation, lower surface: 146D. Petiole length: About 1.5 cm. Petiole diameter: About 4 mm. Petiole color: 146D.

Flower description:

*Flower type and habit.*—Double salverform flowers; flowers face mostly upward or outward; axillary. Very freely flowering habit, about two open flowers and about five to six flower buds per lateral branch at one time.

*Natural flowering season.*—Long day responsive; long flowering period, spring until frost in the autumn; flowering continuous during this period. Plants start flowering about four weeks after planting rooted cuttings. Flowers persistent.

*Flower longevity on the plant.*—About seven days.

*Fragrance.*—Strong; sweet.

*Flower size.*—Diameter: About 7 cm. Tube length: About 3 cm. Throat diameter, distal end: About 3.25 cm. Tube diameter, proximal end: About 7 mm.

*Flower buds.*—Length: About 3.2 cm. Diameter: At apex, about 2.5 cm; at base, about 5 mm. Shape: Elongated oblong with ruffled apices. Color: 145A to 145B.

*Corolla.*—Quantity/arrangement: About five to six outer petals fused in a single shorl, funnelform; interior to the outer whorl, about 21 to 23 progressively smaller petaloids, variable in size. Petal length from throat: About 2.5 cm. Petal width: About 3.5 cm. Petal/petaloid shape: Roughly spatulate or fan-shaped. Petal/petaloid apex: Rounded to acute; ruffled. Petal/petaloid margin: Entire; ruffled. Petal/petaloid texture: Smooth, velvety. Color: Petals/petaloids, upper surface, when opening: 85C. Petals/petaloids, lower surface, when opening: 85D. Petals/petaloids, upper surface, fully opened: 85C; towards apex, 85D; with development, color becoming more white than 155D blushed with 75D. Petals/petaloids, lower surface, fully opened: More white than 155D. Flower throat (inside): 157B. Flower tube (outside): 145C. Venation, upper petal/petaloid surface: 71C. Venation, lower petal/petaloid surface: 145B to 145C. Venation, throat: 148C. Ventation, tube: 145B.

*Sepals.*—Arrangement/appearance: Single whorl of five sepals fused at base, star-shaped. Length: About 1.3 cm. Width: About 4 mm. Shape: Elongated oblong. Apex: Rounded to broadly acute. Margin: Entire. Texture, both surfaces: Pubescent, glandular. Color, upper surface: 146A. Color, lower surface: 146B.

*Peduncles.*—Length: About 2.5 cm. Width: About 2 mm. Angle: About 45 to 60° from the stem. Strength: Strong. Texture: Pubescent. Color: 146B.

*Reproductive organs.*—No reproductive structures observed, all transformed into petaloids; flowers sterile.

*Seed/fruit.*—Seed and/or fruit production has not been observed.

Disease/pest resistance: Plants of the new Petunia have not been noted to be resistant to pathogens or pests common to Petunia.

Garden performance: Plants of the new Petunia have been observed to have good garden performance. Plants of the new Petunia have been noted to tolerate temperatures from 0 to 38° C. and have excellent tolerance to rain and wind.

It is claimed:

1. A new and distinct cultivar of Petunia plant named 'Condolavender', as illustrated and described.

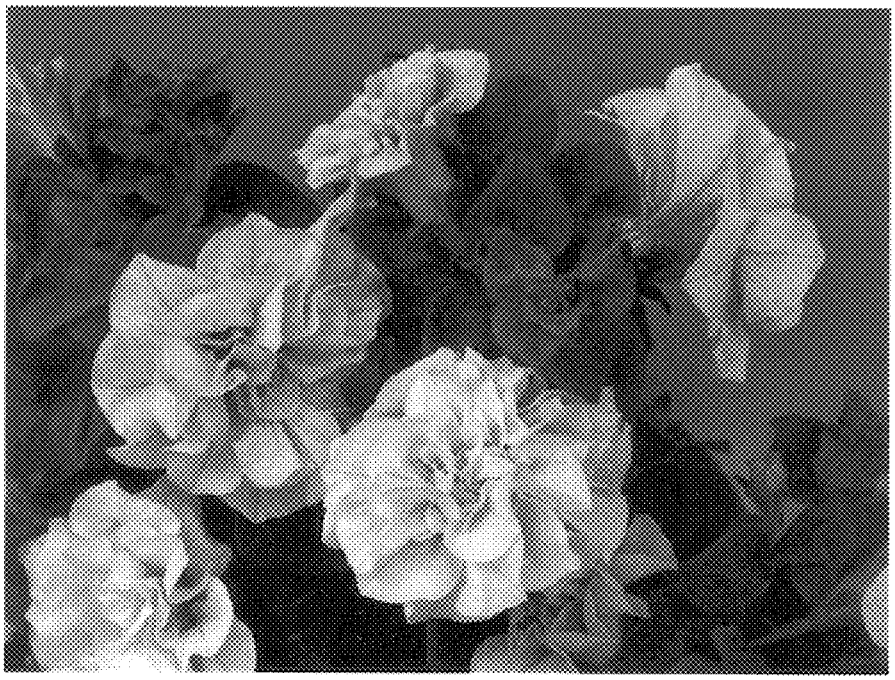
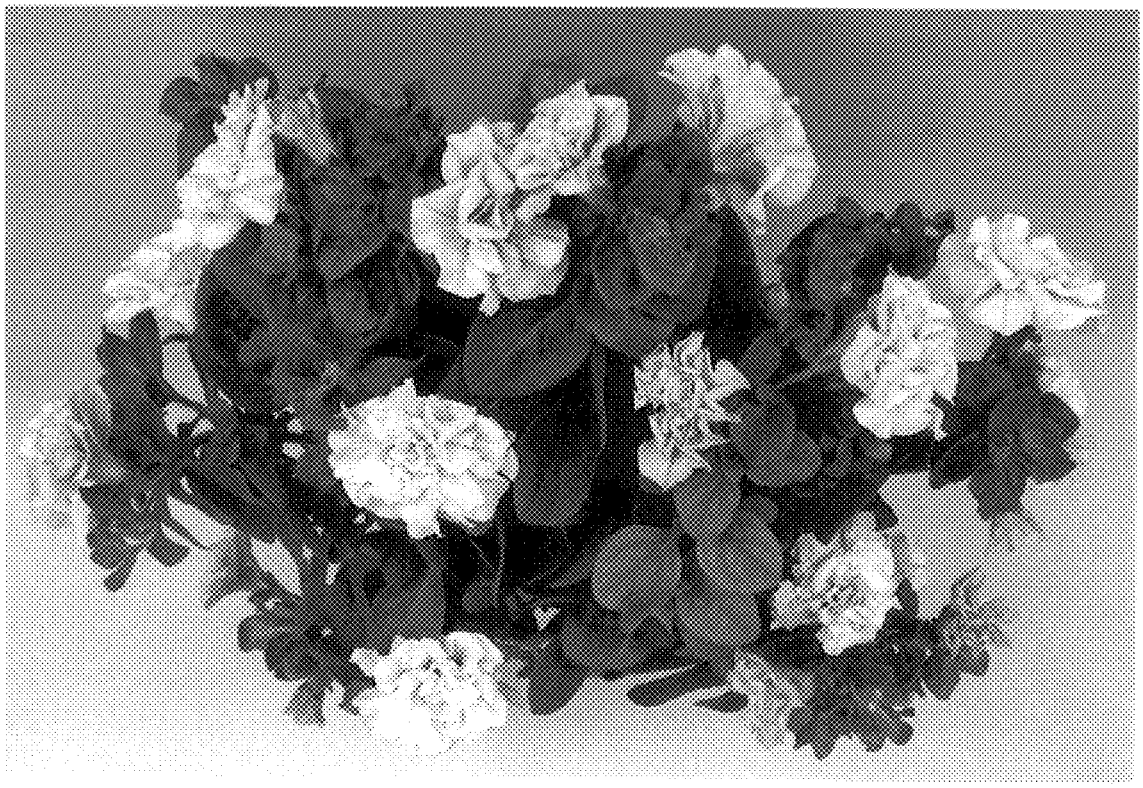

* * * * *